United States Patent [19]

Roane

[11] 4,329,131
[45] May 11, 1982

[54] TNT STATE SENSOR

[75] Inventor: Asa E. Roane, Pulaski, Va.

[73] Assignee: The United States of America as represented by the Secretary of the Army, Washington, D.C.

[21] Appl. No.: 144,746

[22] Filed: Apr. 28, 1980

[51] Int. Cl.³ .............................................. B22D 11/01
[52] U.S. Cl. ........................................ 425/6; 149/105; 264/3 C; 425/136; 425/436 R; 427/8
[58] Field of Search ........................ 149/105; 264/3 C; 425/6, 136, 436 R; 427/8

[56] References Cited

U.S. PATENT DOCUMENTS 1,996,146  4/1935  Crater .................................. 149/105
2,395,856  3/1946  Foster et al. ......................... 149/105

*Primary Examiner*—Stephen J. Lechert, Jr.
*Attorney, Agent, or Firm*—Nathan Edelberg; Robert P. Gibson; Robert O. Richardson

[57] ABSTRACT

Light emitting diodes (LED) are used in conjunction with phototransistors to determine the liquid-solid state of a 0.030–0.040 inch film of trinitrotoluene (TNT). Liquid TNT is collected on the surface of a rotating drum, and is subsequently cooled to a solid film and removed by a "flaking" knife. The emitted beam from the LED is absorbed when the TNT is in the solid state and transmitted to and reflected from the drum surface when the TNT is in the liquid state. The relative intensity of the reflected beam is a measure of the state of the TNT.

10 Claims, 4 Drawing Figures

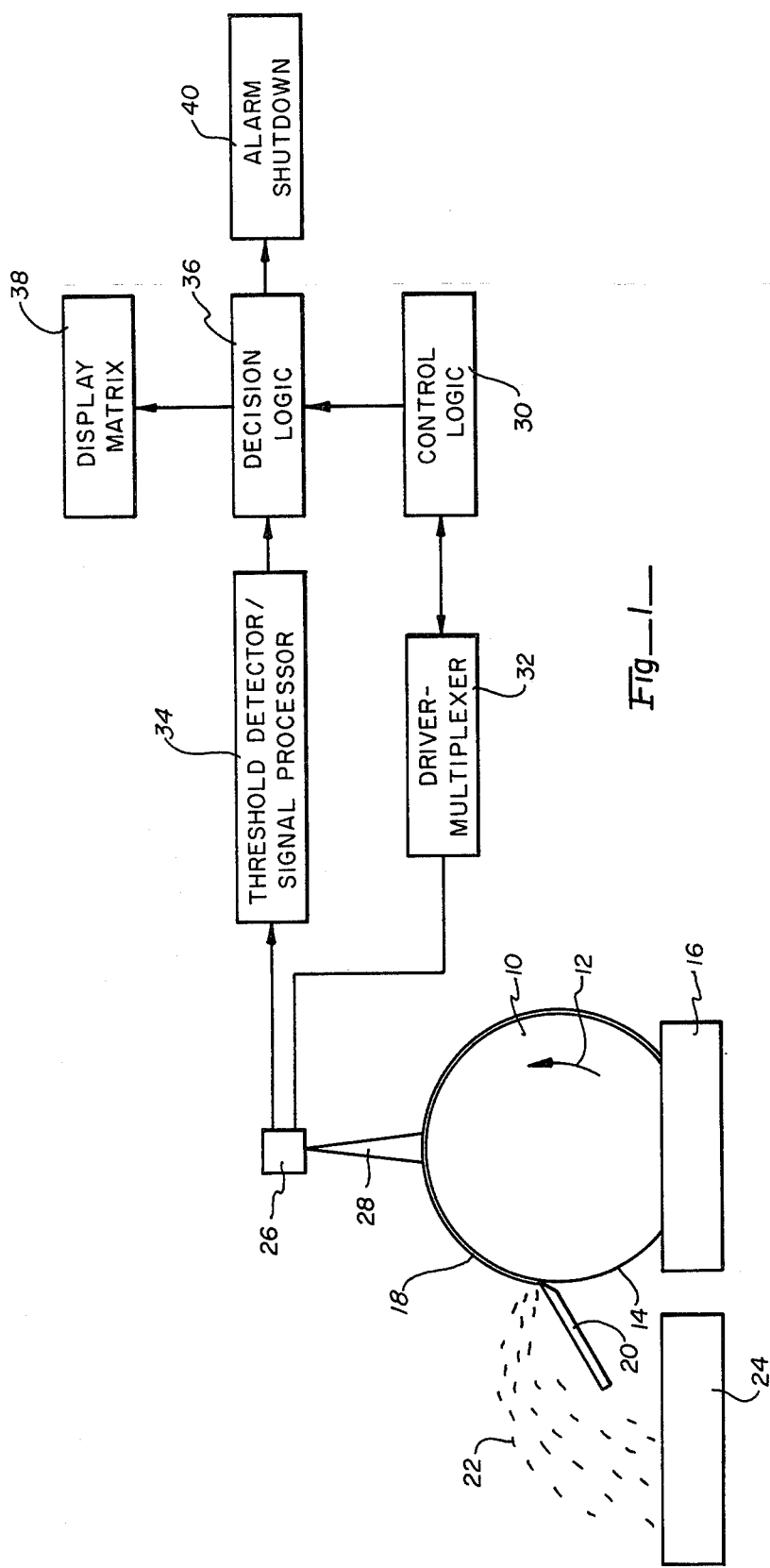

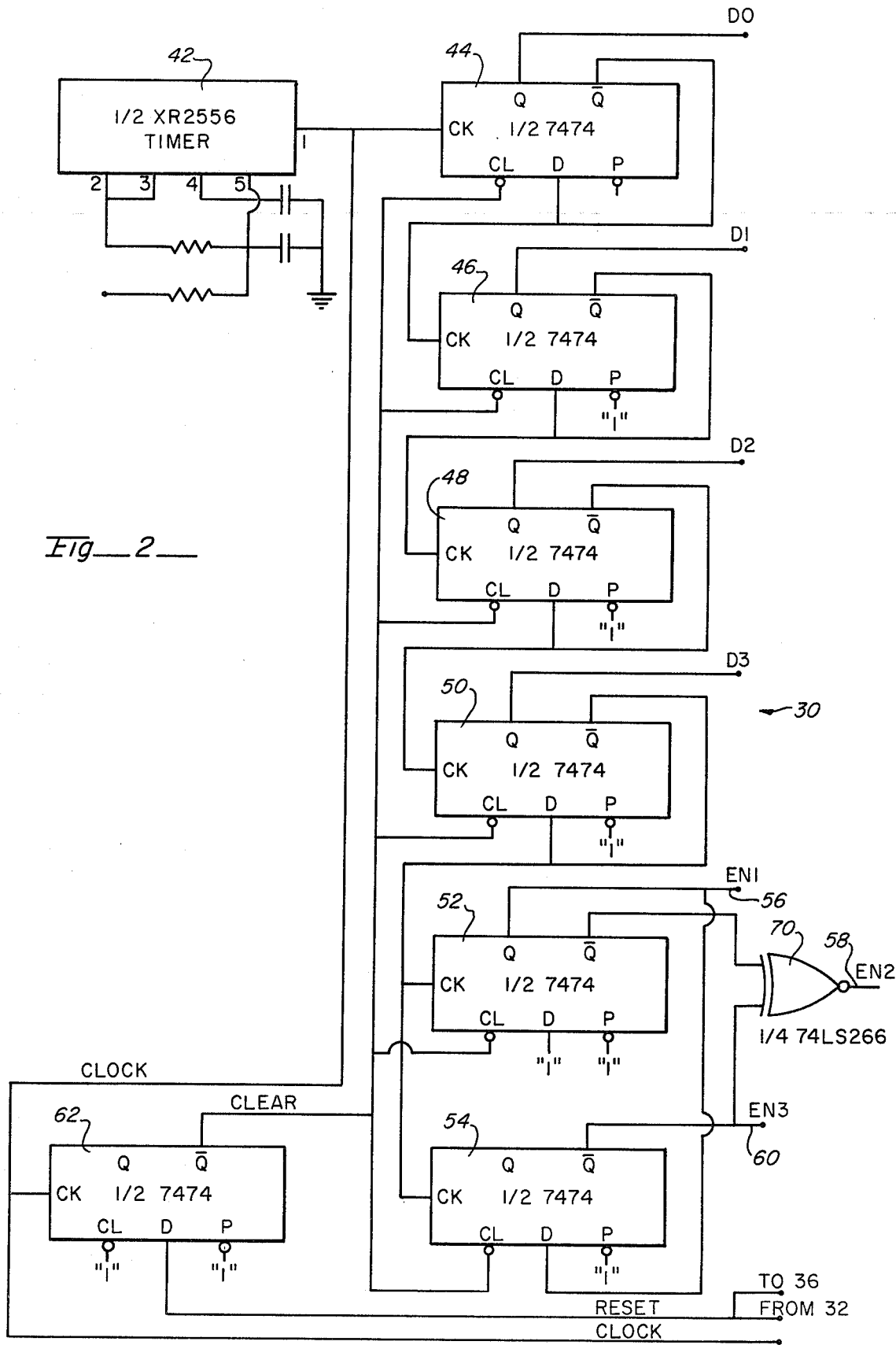
Fig_2

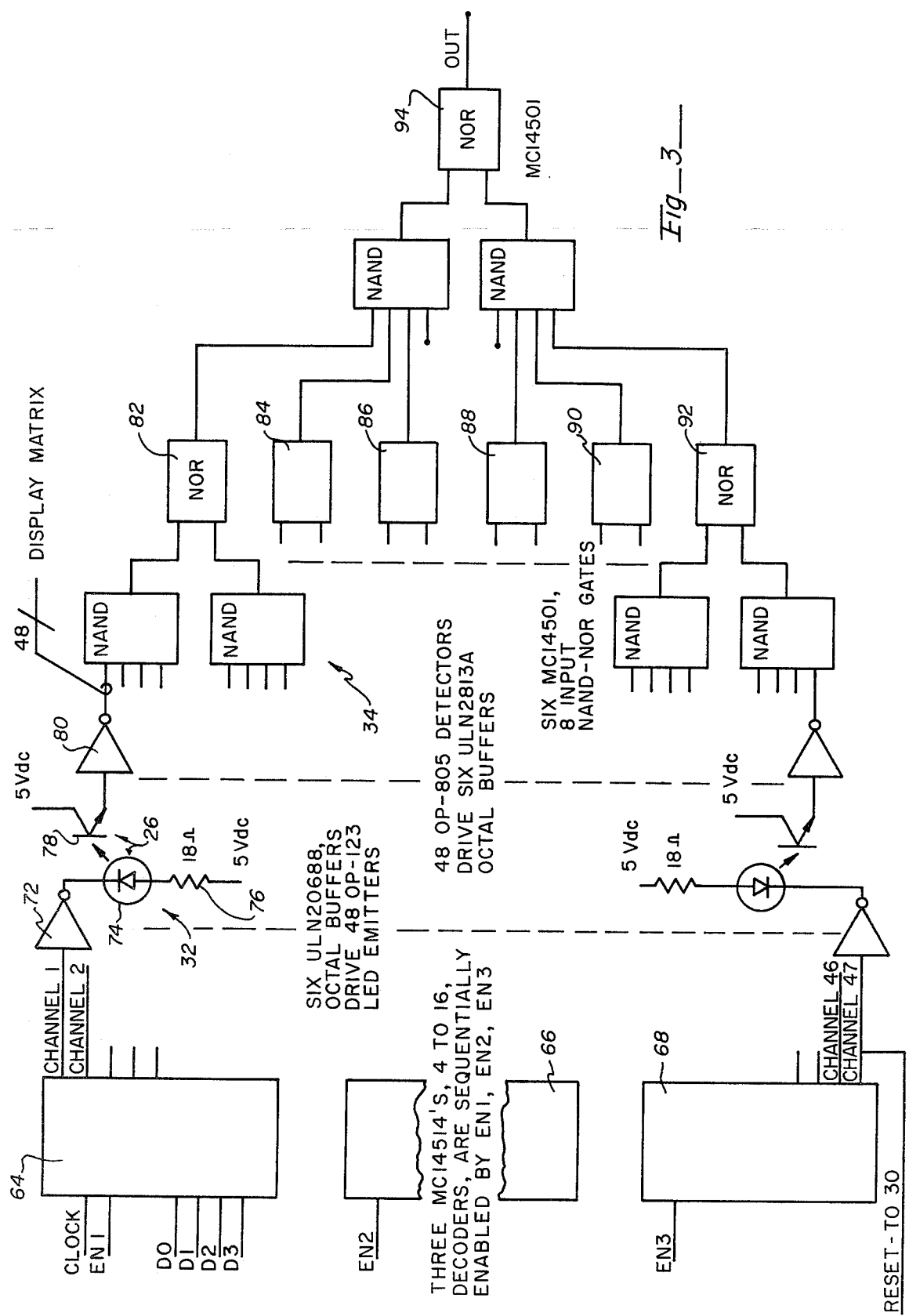

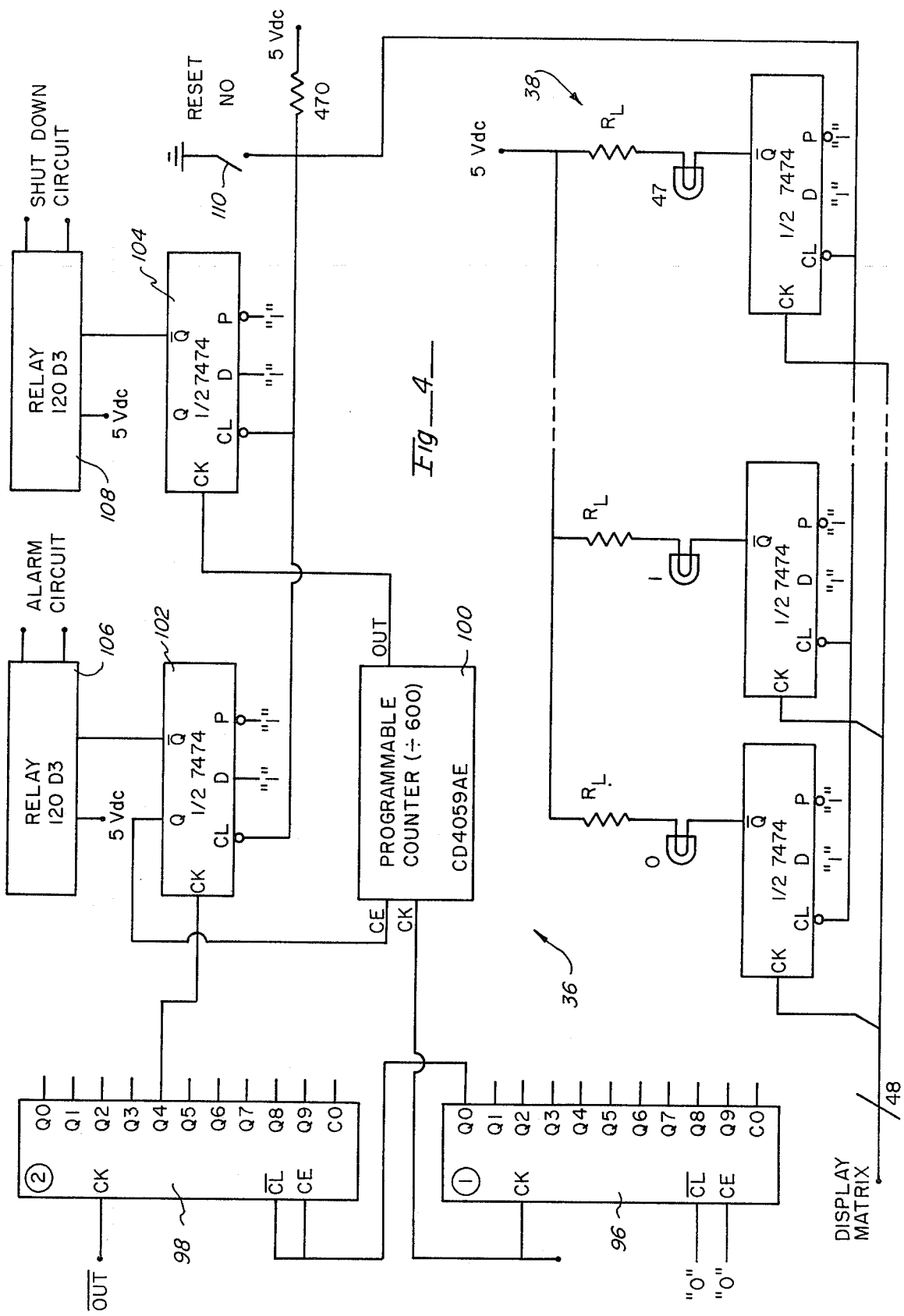
Fig_4_

TNT STATE SENSOR

GOVERNMENT RIGHTS

The invention described herein may be manufactured and/or used by or for the Government for governmental purposes without the payment of any royalty thereon.

BACKGROUND OF THE INVENTION

The last operation in manufacturing TNT is solidification of the TNT into a relatively safe form that accommodates storage/shipment and subsequent reprocessing. The safest form has been found to be flakes as compared to liquid, granules, or blocks. The flake operation consists of a rotating water cooled drum which intercepts the surface of liquid TNT (110° C.). A 0.030–0.040 inch film of liquid adheres to the drum surface, cools is solidification and is removed by a knife. The resulting flakes are collected and the liquid TNT is replenished so as to provide a continuous process. Safe operation of the process and safe handling of the finished product essentially depends on the solid state of the TNT at the knife. The transition state will cause varying degrees of clumping and secondary crystalline growth increases the density of the finished product and thereby increases the hazard associated with handling TNT. Of particular concern is the unwanted growth of single crystal "whiskers" that can initiate an explosion when broken. To maintain the safety factor associated with the process, it is necessary to monitor the state of the TNT i.e., whether it is in liquid or solid form, prior to flaking and to shut down the process when a threshold of liquidity is measured.

SUMMARY OF THE PRESENT INVENTION

The TNT State Sensor, in accordance with the present invention, utilizes light emitting diodes which emit a 20° beam of infrared light having a wavelength of 940 nanometers (nm). The beam is transmitted thru the liquid film of TNT, reflected from the flaker drum surface and detected by a compatible phototransistor. When the film is in the solid state, the infrared beam is effectively attenuated. The relative intensity of the reflected beam, as detected by the phototransistor, triggers a GO/NO-GO threshold detector. The drum is scanned by a row of 48 emitter/detectors which is positioned eight inches from the drum surface and parallel to its longitudinal axis. The 48 channels are in turn scanned at a fundamental frequency of 1 kilohertz (Khz) by a multiplexer and the resulting digital information is processed by random/sequential logic. The logic determines when a warning alarm should be sounded and shuts down the process after 30 seconds unless the operator overrides the unit. A visual display of each channel is included to verify indications and to aid troubleshooting.

It has been determined that near infrared light, 940 nm wavelength, is substantially diffused or absorbed by a solid TNT film, but is not reflected or absorbed by a liquid TNT film. The present invention exploits this characteristic by measuring the relative intensity of the beam reflected from the polished drum surface. The TNT State Sensor must be manually reset during start-up since a bare drum surface will be detected as a liquid TNT film. Other devices which operate at green, yellow and orange frequencies (600 nm) provided a smaller noise margin. As a result, OPTRON's infrared OP132 emitters and OP805 detectors were used. Both devices have a −3 decibel (dB) power beam width of 20°. The emitters are energized for 1.0 milliseconds (m sec) at a current of 0.2 amperes direct current (Adc). The peak power emitted by the OP132 at 0.2 Adc is 6 Milliwatts (mw). Solid state devices are inherently safe for application in an explosive environment. The storage capacity of the cable harness and the power dissipated by the emitters represent a potential hazard. A substantial design safety margin was achieved by limiting these characteristics to 1700 picofarads (pf) and 0.2 watt respectively. The peak power density impinging the TNT film is 1.0 milliwatts per square inch (mw/in$^2$) and the duty cycle is 2%.

The 48 emitter/detectors provide a detection band 60 inches long (drum length) and 2.18 inches wide. This spaces the emitters 1.236 inches center to center with the corresponding detector placed ¼ inch away. A drum radius of 24 inches and an angular velocity of 50 radians/minute provides a surface velocity of 20 inches/second. The fundamental frequency of 1 Khz scans the 48 channels at a 20 Hz frequency. Thus, the entire drum surface is scanned prior to flaking.

The control logic consists of a 1 Khz clock, a 4-bit counter, a 2-bit counter with three decoded "enable" lines, and a 1-clock period scan reset circuit which clears the counters and syncronizes the decision logic. The counter outputs are decoded by three 4 to 16 latched multiplexers into 48 lines which "enable" the LED drivers. The outputs of the phototransistors are buffered by high input impedance darlington amplifers. The turn-on threshold of the darlington provides a convenient detection level which reasonably correlates to the state of the TNT film.

The darlington outputs are OR'ed by a series of NAND-NOR gates to obtain a single detect output. The decision logic, which is implemented using sequential logic, operates upon the detect output. It consists of two decade counters having decoded outputs, a programmable counter, and two data-type flip-flops to latch the alarm and shutdown events. These functions provide for implementation of a wide range of decision schemes. The scheme depicted by the present invention notifies the operator audibly and visually of an indication, and expects the operator to respond within 30 seconds, otherwise the operation is shutdown. Decade counter No. 1 divides the scan reset line by ten. The output resets decade counter No. 2 which counts the number of indications sensed by the 48 phototransistors. A data-type flip-flop is set when four indications are counted. This flip-flop triggers an audible alarm and initializes the programmable counter. If the operator does not reset the alarm flip-flop within 30 seconds, the counter, which counts the scan reset pulses, will set the shutdown flip-flop and the operation will stop. This logic can be reconfigured to automatically reset the alarm in the event that a random hot spot of acceptable size is encountered. However, the reliability of the unit and actual performance boundaries must be firmly established before an automatic decision scheme can be safely implemented. Presently, the unit will accept up to 3 indications out of 480 samples (10 scans) and sound the alarm when four or more indications occur.

The pulsed output signals from the darlington buffers are latched by data-type flip-flops which drive indicator lamps. The straight line matrix of 48 lamps provide a simple verification of the indications detected by the unit. These output signals can be easily interfaced with a thermal dot printer to provide a facsimile of the drum surface whenever an alarm is sounded.

BRIEF DESCRIPTION OF DRAWINGS

FIG. 1 is a schematic view illustrating the TNT state sensor operation,

FIG. 2 is a schematic illustration of the control logic circuit,

FIG. 3 is a schematic illustration the driver-multiplexer, emitter/detector and threshold detector circuits, and FIG. 4 is a schematic illustration of the decision logic display matrix, and alarm shutdown interface circuits.

DESCRIPTION OF PRESENT INVENTION

The TNT State Sensor, in accordance with the present invention, utilizes light emitting diodes (LED) in conjunction with phototransistors to sense the state of a 0.030–0.040 inch film of trinitrotoluene (TNT). The last operation in manufacturing TNT is solidification into a relatively safe form that accommodates storage/shipment and subsequent reprocessing. The safest form has been found to be flakes. The flaking process uses a rotating water cooled drum which intercepts the surface of liquid TNT at 110° C. A thin film of liquid adheres to the drum, cools and is removed by a knife. The resulting flakes are collected and the liquid TNT is replenished so as to provide a continuous process. Safe operation of the process and safe handling of the finished product depends on complete solidification of the TNT prior to flaking. Otherwise, clumping and secondary crystalline growth will result. To maintain the safety factor of the process, it is necessary to monitor the state of the TNT film prior to flaking and to shut down the process when a threshold of liquidity is detected.

Referring now to FIG. 1 there is shown a water cooled drum 10 rotating in the direction shown by arrow 12. As the drum surface 14 passes through the liquid TNT in container 16 a thin film adheres to the drum surface and cools to a solid state film 18. A flaking knife 20 shaves the film into flakes 22 which fall into container 24. The drum 10 is 60 inches in length and 48 inches in diameter. An angular velocity of 50 radians/minute (8 rpm) provides a surface velocity of 20 inches/second. The TNT State Sensor must therefore examine 1200 in$^2$/sec. This was accomplished by scanning the drum surface by a row of 48 LED emitters and 48 phototransistor detectors that is positioned 8 inches from the drum surface. The 48 emitter/detectors are positioned on a support 26. The beam 28 emitted from the LED is transmitted through a liquid TNT film and reflected from the drum surface 14, or in the alternative, the beam is diffused/absorbed by a solid TNT film.

The control logic circuits 30, driver-multiplexer 32, threshold detector/signal processor circuits 34, decision logic circuits 36, display matrix 38 and alarm, shutdown circuits 40 are, as individual components, conventional and within the present state of the art. Accordingly, since this presents a working embodiment to enable one skilled in the art to practice the invention, the descriptions of these circuits will be briefly given.

The control logic circuits 30 are shown in FIG. 2. The control logic consists of a 1 Khz clock 42, a 4-bit counter 44, 46, 48, 50, a 2-bit counter 52, 54 with three decoded "enable" lines 56, 58, 60, a 1-clock period scan reset flip-flop 62, and three latched 4 to 16 decoders 64, 66, 68. The clock 42 is implemented by an EXAR XR2556 timer configured as an astable multivibrator. The 4-bit counter 44, 46, 48, 50 is implemented by 4 data-type flip-flops (7474) in a ripple configuration having data outputs denoted as D$\phi$, D1, D2 and D3. The 2-bit counter 52, 54 is implemented by 2 data-type flip-flops in a ripple configuration having three decoded "enable" outputs denoted as EN1, EN2 and EN3. A single exclusive-nor gate 70 facilitates decoding. The 1-period scan reset circuit 62 is implemented by a data-type flip-flop in a clocked set-reset mode. This flip-flop is set when channel 47 (in FIG. 3) is enabled and is reset on the following clock pulse. The data and enable outputs are decoded by three 4 to 16 demultiplexers 64, 66, 68 (Motorola MC14514) to 48 channels.

The driver-multiplexer circuit 32, among other circuits, is schematically depicted in FIG. 3. Each channel from demultiplexers 64, 66, 68 enables a high current buffer 72 (Unilogic ULN2068B) which drives an OPTRON OP132 LED emitter 74. The drive current is limited by an 18 OHM resistor 76. The decoded output of channel 47 is used as a convenient scan reset.

It has been determined that near infrared frequencies provided optimal performance. As a result, OPTRON'S OP132 emitters 74 and OP805 detectors 78 were selected for the emitter/detector circuit 26. Both are infrared devices (940 nm and 840 nm respectively) that have a 3dB power beam width of 20°. The frequency mismatch desensitizes and emitter/detector pair by approximately 2dB. The emitters are multiplexed at a fundamental frequency of 1 Khz to achieve a row scan frequency of 20 hz. Each emitter 74 is selectively energized for 1 m sec during every 49 m sec scan. A 5 Vdc power supply and an 18 ohm current limiting resistor 76 establishes a current of 0.2 Adc. At this operating point the LED's 74 emit a peak power of 6 mw which results in a peak power density of 1 mw/in$^2$ at the drum surface. The dynamic range of light intensity received by the detectors, in conjunction with the frequency decoupling of the emitters, as the TNT film passes from the liquid state to the solid state permits direct coupling of the detectors or phototransistors 78 to a darlington buffer 80. The darlington is a convenient threshold detector.

The threshold detector/signal processor circuits 34 includes the directly coupled darlington buffers 80 (Unilogic ULN2813A) and seven NAND-NOR gates 82, 84, 86, 88, 90, 92 and 94. The operating points of the emitters 74 and of the detectors 78 in conjunction with their optical coupling when the TNT is liquid, provides a 1–2 mA signal to the buffers 80. This level is sufficient to drive the buffers into the "1" state with a minimal margin. A 6dB attenuation of this signal be decreased optical coupling will drive the buffers into the "0" state. It was empirically determined that the optical coupling is not attenuated by the film until late in the TNT transition stage. As a result, the physical controlling factors which govern cooling of the film guarantee that a solid film 18 exists at the knife 20 when the phototransistor output falls below the "turn-on" threshold of the darlington buffer 80. The 48 channels are processed by using negative logic and two levels of NAND-NOR gates (Motorola MC14501) 82, 84, 86, 88, 90, 92, 94 to provide a single NOR'ed output, $\overline{OUT}$. This digital signal can be described as Non-Return to Zero (NRZ) data having a 300 nanoseconds (nsec) glitch at the bit boundary due to a rise time and fall time difference in the emitters' 74 output. When the film 18 is in the solid state, the $\overline{OUT}$ signal will be in the "1" state, and when the film is in the liquid state, the $\overline{OUT}$ signal will be in the "0" state with 300 nsec pulses at the bit boundary. This signal could be readily converted to true NRZ data by employing a data-type flip-flop triggered by the trailing edge of the clock signal. Although this would accommodate digital processing, it was not necessary for the processing scheme implemented.

The decision logic circuit 36 consists of two decade counters 96, 98 having decoded outputs, a programmable counter 100, and two data-type flip-flops 102, 104 to latch the alarm and shut down events. The decision scheme presently implemented is schematically depicted in FIG. 4. It notifies the operator audibly and visually of an indication, and expects the operator to respond within 30 seconds, otherwise the operation is shutdown. Referring to FIG. 4, decade counter No. 1 Motorola (MC14017), i.e., 96, divides RESET by 10. The output periodically resets decade counter No. 2, 98, (MC14017) which counts the number of indications sensed by the 48 phototransistors. Each indication represents a circular area (6 in$^2$) on the drum surface that is detected as being in the liquid state. A data-type flip-flop 102 (7474) is set when four indications are counted. This flip-flop drives a solid state relay 106 and enables the programmable counter 100. This counter (Motorola CD4059AE) divides the 20 hz RESET signal by 600 to provide a 30 second time delay. A data-type flip-flop (7474) 104 is set after 600 drum scans. This flip-flop drives a solid state relay 108. This logic can be reconfigured to automatically reset the first flip-flop in the event that a random but spot of acceptable size is encountered. However, the reliability of the unit and actual performance boundaries must be firmly established before an automatic decision scheme can be safely implemented. Presently, the unit will accept up to 3 indications out of 480 sample (10 scans) and will be activated when 4 or more indications occur.

The TNT State Sensor provides for interactive process control via three outputs: a visual display, a warning alarm, and a shut down relay. The output of each detector buffer is latched by a data-type flip-flop which drives an indicator lamp. The resulting display matrix 38 provides visual status for the 48 emitter/detector channels. This display enables the operator to interact with the sensor by manually activating the RESET switch 110. The display matrix is schematically depicted in FIG. 4. When the sensor is activated, 4 or more indications, an alarm is triggered by the first solid state relay. A shut down relay is triggered 30 seconds after activation. The operator can clear the display and deactivate (reset) the sensor by momentarily pushing a reset switch 110.

The invention in its broader aspects is not limited to the specific combinations, improvements and instrumentalities described but departures may be made therefrom within the scope of the accompanying claims without departing from the principles of the invention and without sacrificing its chief advantages.

I claim:

1. A TNT State Sensor for a rotating drum having a reflective surface rotating through liquid TNT to develop a TNT film on said drum, said sensor comprising:

a light emitter beaming light toward the surface of said drum, said light having a frequency such that it propogates substantially undiminished through liquid TNT on said drum and substantially does not propogate through or reflect from TNT in a solid film state on said drum, and a detector sensing light reflected from said drum through said liquid TNT.

2. A TNT State Sensor as in claim 1 wherein said drum is cooled to cause said liquid TNT to become a solid state film.

3. A TNT State Sensor as in claim 2 wherein said solid state film is scraped into flakes with a flaking knife applied to said surface.

4. A TNT State Sensor as set forth in claim 3 wherein said light emitter beams light onto said drum surface at points thereon prior to scraping at said points with said flaking knife.

5. A TNT State Sensor as set forth in claim 1 wherein said light is in the infrared light wavelength.

6. A TNT State Sensor as set forth in claim 1 wherein indicator means responds to light reflection through liquid TNT on said drum.

7. A TNT State Sensor as set forth in claim 6 wherein shut down means stops drum rotation a predetermined time after an indicating response is made unless such shut down means is inactivated by an operator.

8. A TNT State Sensor as set forth in claim 1 wherein emitter/ detectors are spaced across the length of said drum, the emitters of which are sequentually energized, and alarm means responsive to a predetermined rate of light receptions by said detectors.

9. A TNT State Sensor as set forth in claim 8 wherein 48 emitter/detectors provide a detection band 60 inches long, said emitters being sequentually energized once per scan, and said alarm means responds to four or more light detections by said detectors in 10 scans of said emitters.

10. A TNT State Sensor as set forth in claim 9 wherein a display matrix indicates those detectors having light detections.

* * * * *